(12) United States Patent
Price

(10) Patent No.: US 8,696,642 B1
(45) Date of Patent: Apr. 15, 2014

(54) MALE DISPOSABLE INCONTINENCE DIAPER

(76) Inventor: Mark A. Price, Auburn, CA (US)

( * ) Notice: Subject to any disclaimer, the term of this patent is extended or adjusted under 35 U.S.C. 154(b) by 274 days.

(21) Appl. No.: 13/099,889

(22) Filed: May 3, 2011

(51) Int. Cl.
*A61F 13/15* (2006.01)

(52) U.S. Cl.
USPC .................................................. 604/385.09

(58) Field of Classification Search
USPC ........................................ 604/385.09, 395
See application file for complete search history.

(56) References Cited

U.S. PATENT DOCUMENTS

| | | | | |
|---|---|---|---|---|
| 2,837,095 A * | 6/1958 | Stevenson | | 604/354 |
| 3,903,571 A * | 9/1975 | Howell | | 24/436 |
| 4,615,695 A | 10/1986 | Cooper | | |
| 4,944,733 A * | 7/1990 | Casale | | 604/385.09 |
| 5,219,219 A * | 6/1993 | Virdin, Jr. | | 383/4 |
| 5,380,310 A * | 1/1995 | Mitrani | | 604/385.201 |
| 5,383,867 A * | 1/1995 | Klinger | | 604/385.23 |
| 5,618,279 A | 4/1997 | Pudlo | | |
| 5,669,902 A * | 9/1997 | Sivilich | | 604/396 |
| 5,836,057 A * | 11/1998 | Machfud | | 24/400 |
| 5,843,065 A | 12/1998 | Wyant | | |
| 5,864,890 A * | 2/1999 | Niedermeyer | | 2/403 |
| 5,916,202 A * | 6/1999 | Haswell | | 604/356 |
| 5,984,910 A * | 11/1999 | Berke | | 604/352 |
| 6,183,458 B1 * | 2/2001 | Ahlstrand et al. | | 604/385.19 |
| 6,419,665 B1 * | 7/2002 | Cohen | | 604/349 |
| 6,443,341 B1 * | 9/2002 | Rittmann | | 224/219 |
| 6,502,285 B2 * | 1/2003 | Kiely | | 24/433 |
| 7,029,178 B2 * | 4/2006 | Gzybowski | | 383/64 |
| 7,658,732 B2 * | 2/2010 | Van Gompel et al. | | 604/385.22 |
| 8,245,364 B2 * | 8/2012 | Ackerman et al. | | 24/400 |
| 8,291,682 B2 * | 10/2012 | Dodson et al. | | 54/66 |
| 2001/0044991 A1 * | 11/2001 | Graves | | 24/400 |
| 2002/0099346 A1 * | 7/2002 | Strobl | | 604/367 |
| 2003/0028161 A1 * | 2/2003 | Carballo | | 604/349 |
| 2004/0261156 A1 * | 12/2004 | Lewis et al. | | 2/227 |
| 2006/0259000 A1 * | 11/2006 | Bailey et al. | | 604/385.09 |
| 2008/0007940 A1 * | 1/2008 | Cheng | | 362/103 |
| 2009/0144948 A1 * | 6/2009 | Jeon | | 24/403 |
| 2011/0163095 A1 * | 7/2011 | Kitai | | 220/212 |

\* cited by examiner

*Primary Examiner* — Susan Su

(57) ABSTRACT

A male disposable incontinence diaper with re-sealable vertical aperture, the aperture consisting of a plastic slider operatively engaging two intermarrying plastic seams which are alternatively locked and closed when the slider is in a first position, and open and unlocked when the slider is in a second position, the aperture enabling the wearer to access his penis and urinate outside the diaper without having to first remove the diaper. The plastic slider and intermarrying plastic seams maintain a watertight seal when closed, thus protecting the wearer of the diaper from the leakage of bodily fluids accidentally discharged into the diaper.

7 Claims, 3 Drawing Sheets

MALE DISPOSABLE INCONTINENCE DIAPER

BACKGROUND OF THE INVENTION

Various types of male disposable incontinence diapers are known in the prior art. However, what is needed is a male disposable incontinence diaper that includes a re-sealable vertical aperture situated in the front of the diaper so the wearer may urinate through the aperture as desired.

FIELD OF THE INVENTION

The present invention relates to a male disposible incontinence diaper, and more particularly, to a male disposable incontinence diaper that includes a re-sealable vertical aperture situated in the front of the diaper.

SUMMARY OF THE INVENTION

The general purpose of the present male disposible incontinence diaper, described subsequently in greater detail, is to provide a male disposible incontinence diaper which has many novel features that result in a male disposible incontinence diaper which is not anticipated, rendered obvious, suggested, or even implied by prior art, either alone or in combination thereof.

Many male disposible incontinence diapers are known in the prior art but what is needed is a diaper that combines the capture and absorbency features of diapers in general with a re-sealable vertical aperture through which the wearer may urinate in the normal fashion by opening the aperture to urinate outside the diaper.

The vertical aperture has been configured to be impervious to bodily fluids when closed, thereby maintaining the purposefulness of the diaper for treating incontinence, while allowing for directed urination as preferred. The vertical aperture is made impervious to fluids by means of a zip lock plastic seal, interlocking two plastic seams with the action of a slider. When closed, the diaper functions to absorb and capture any discharge of bodily fluids thereby protecting the outer garments of the wearer from unintentional soiling. When the aperture is opened, however, the penis of the wearer may be accessed therethrough and urination may occur in the normal fashion, directed away from the wearer and his clothes. As such, the male disposible incontinence diaper here presented is a device convenient for men suffering from incontinence who are still active in day to day society. The need to undo and remove a diaper without the aforementioned aperture, in the hopes of urinating intentionally, can be embarrassing and cumbersome. Furthermore, the delay caused in removing such a diaper may result in the occurrence of an unintentional discharge, precipitating the very outcome the diaper was designed to protect against. Therefore, the present invention has been devised to allow an incontinent male relative freedom to interact with society as preferred while protecting against the unintentional discharges that affect incontinent males.

While some disposable diapers are noted in the prior art that have various kinds of apertures to address this problem, and allow the wearer to access the penis to urinate when desired, no other diaper is known that has a re-sealable aperture secured and made impervious to fluids by means of an interlocking plastic zip lock.

The present male disposible incontinence diaper can be configured to various sizes appropriate for males of different ages. The present device is therefore useful for potty training young adults and toddlers who are learning how to urinate in the normal fashion, standing erect and consciously directing their urine stream, while protecting against the unintentional discharge of bodily fluids which may also result.

Thus has been broadly outlined the more important features of the present male disposible incontinence diaper so that the detailed description thereof that follows may be better understood and in order that the present contribution to the art may be better appreciated.

Objects of the present male disposible incontinence diaper, along with various novel features that characterize the invention are particularly pointed out in the claims forming a part of this disclosure. For better understanding of the male disposible incontinence diaper, its operating advantages and specific objects attained by its uses, refer to the accompanying drawings and description.

BRIEF DESCRIPTION OF THE DRAWINGS

Figures

DETAILED DESCRIPTION OF THE DRAWINGS

Figure 1:
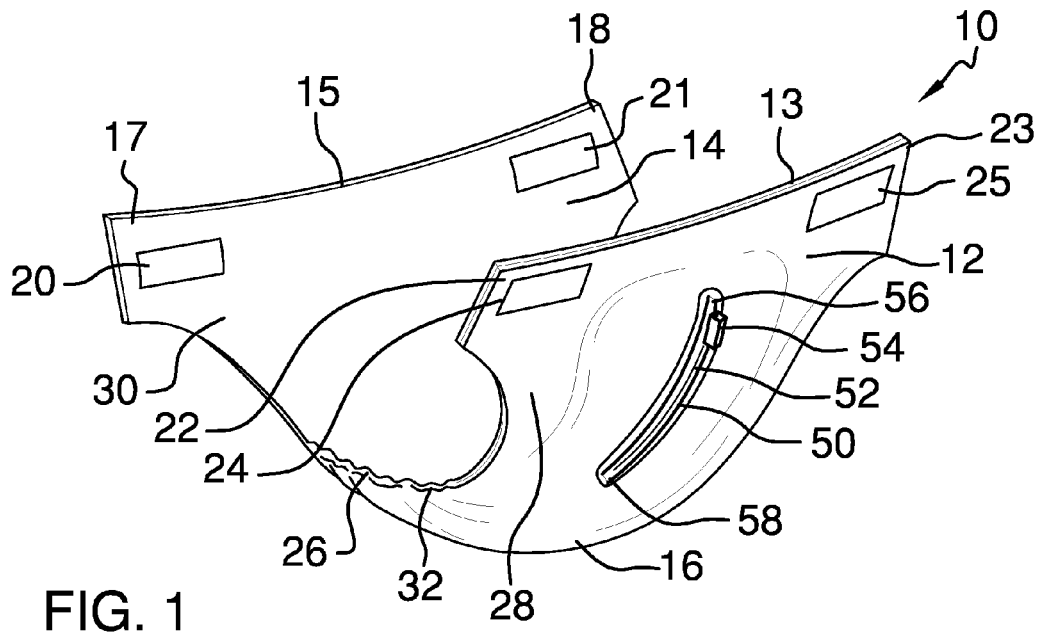
FIG. 1 is an isometric view.
Figure 2:
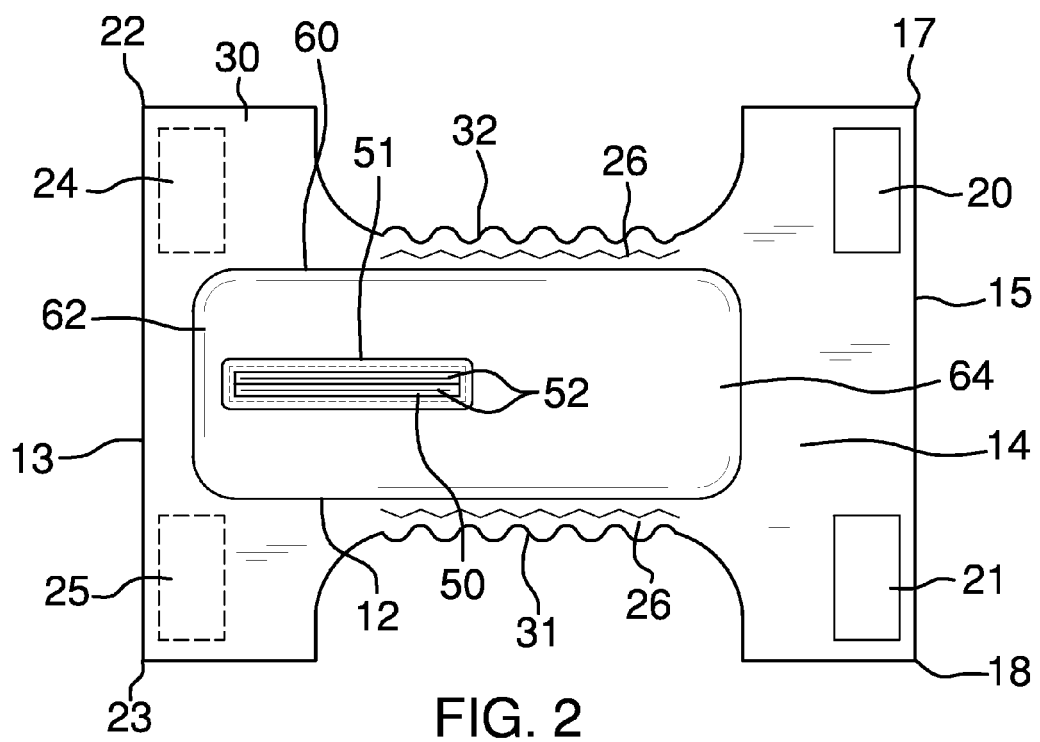
FIG. 2 is a bottom plan view showing an interior surface.
Figure 3:
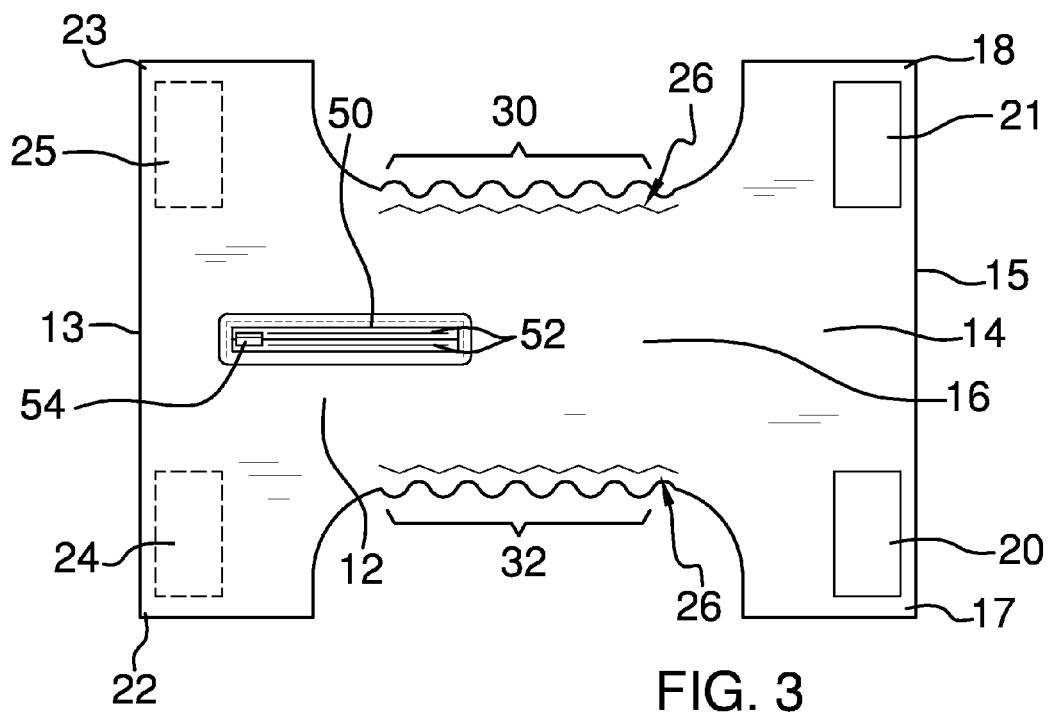
FIG. 3 is a top plan view showing an exterior surface.
Figure 4:
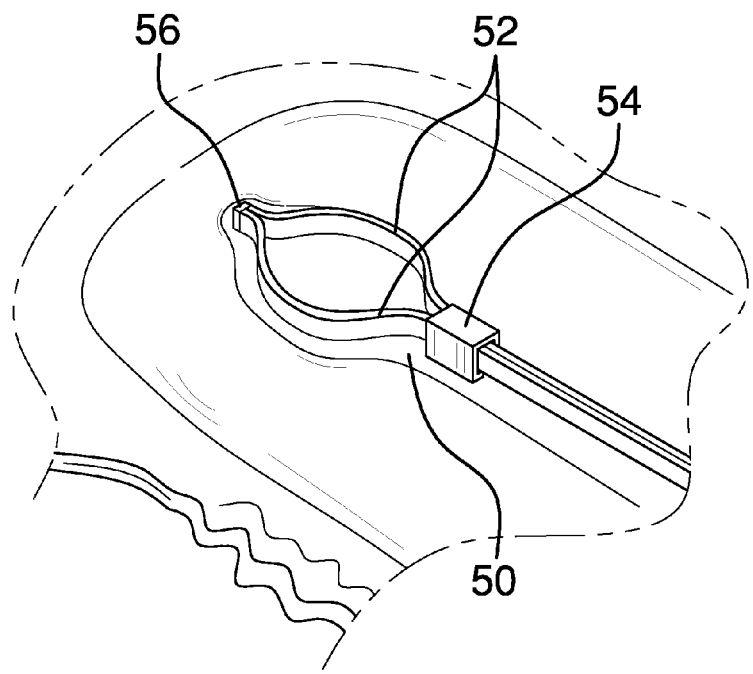
FIG. 4 is a detail view of a zip lock seal.
Figure 5:
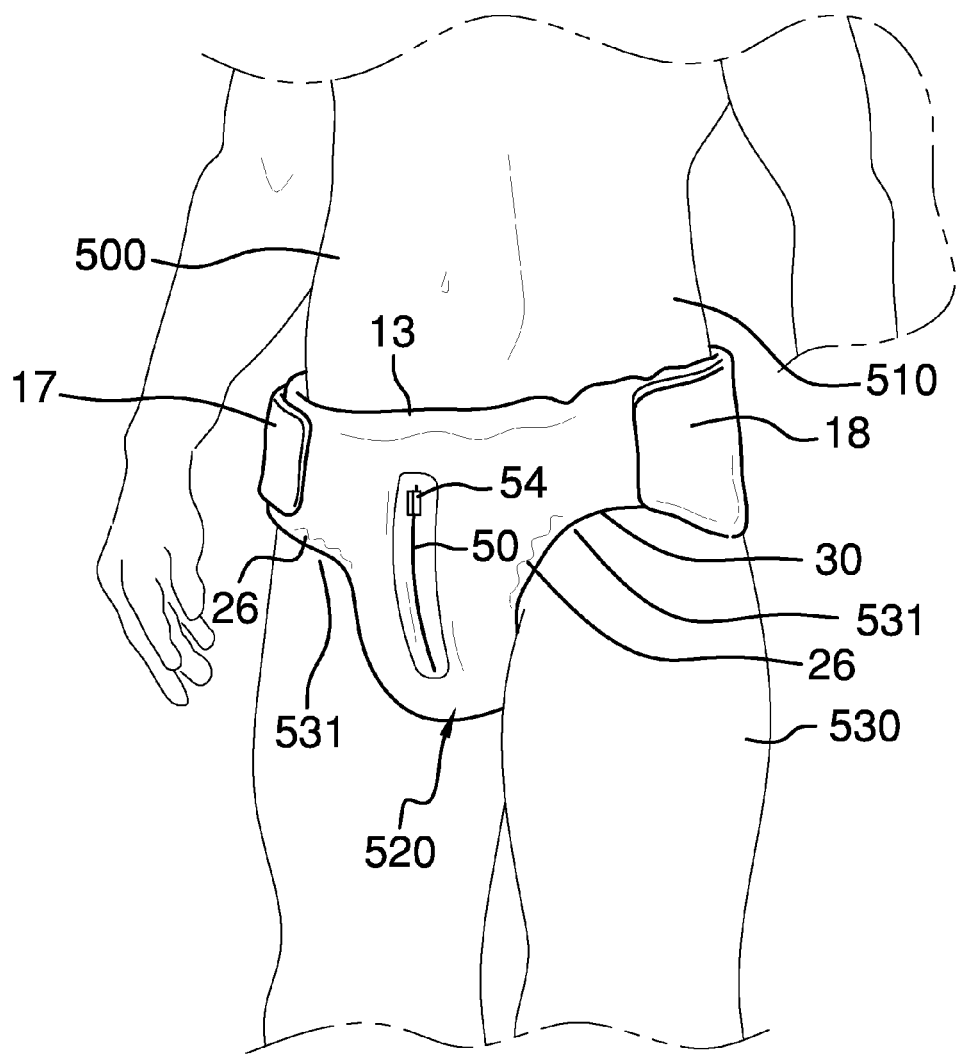
FIG. 5 is an in use isometric view.

With reference now to the drawings, and in particular FIGS. 1 through 5 thereof, example of the male disposable incontinence diaper employing the principles and concepts of the present male disposable incontinence diaper and generally designated by the reference number 10 will be described.

Referring to FIGS. 1 through 5 a preferred embodiment of the male disposable incontinence diaper 10 is illustrated.

The male disposable incontinence diaper 10 includes a front portion 12, a rear portion 14 and a groin portion 16 disposed between the front portion 12 and the rear portion 14. The diaper front portion 12, the rear portion 14, and the groin portion 16 are formed of a material impervious to liquids in general, and specifically impervious to bodily fluids. The front portion 12, rear portion 14 and groin portion 16 are configured to gird the hips 510 and a groin 520 of a male human 500 wearing the diaper 10 and further encircle the upper end 531 of legs 530 of a male human 500 wearing the diaper 10.

The male disposable incontinence diaper 10 has an exterior surface 28 and an interior surface 30. The interior surface 30 is configured to be continuous contact with the wearer 500. The diaper 10 also has a front edge 13 and a rear edge 15 connected by a first side edge 31 and a second side edge 32 at four corners 17, 18, 22 and 23.

The diaper 10 has four corners 17, 18, 22, and 23. A pair of front attachment bodies 24, 25 and a pair of rear attachment bodies 20, 21 are also provided. Each of the front attachment bodies 24, 25 are disposed proximal to the corners 22, 23 on the front edge 13. Each of the rear attachment bodies 20, 21 are disposed proximal to corners 17, 18 on the rear edge 15. The front attachment bodies 24 and 25 are disposed on the exterior surface 28 and the rear attachment bodies 20 and 21 are situated on the interior surface 30. The front attachment bodies 24 and 25 overlap the rear attachment bodies 20 and 21 when the diaper 10 is worn, and attached thereto, such that the front edge 13 and the rear edge 15 then form a continuous waistband that encircles the waist 510 of the wearer 500. In a preferred embodiment, the front 24 and 25 and rear 20 and 21 attachment bodies are parallelepiped sticky pads which adhere to each other when the diaper 10 is worn.

An amount of elastic 26 is continuously disposed along the first side edge 31 and the second side edge 32 and conforms the first side edge 31 and the second side edge 32 to the legs 530 of the wearer 500. The elastic 26 ensures a snug fit between the diaper 10 and the wearer 500 to maintain a watertight seal between the diaper 10 and the wearer 500 thereby capturing and containing any bodily fluids discharged into the diaper 10.

An absorbent pad 60 is continuously disposed within the front portion 12 and the groin portion 16 along a central vertical axis of the interior surface 30. The pad 60 may be parallelepiped. The pad 60 absorbs bodily fluids discharged thereon thereby holding the fluids away from the wearer 500 until the diaper 10 is removed and disposed. The pad 60 has an anterior end 62 and a posterior end 64.

A re-sealable aperture 50 is centrally disposed along a central vertical axis of the pad proximal to the pad 60 anterior end 62. The aperture 50 is disposed to be proximal to the male genitalia when the diaper 10 is worn. The vertical aperture 50 includes a zip lock mechanism 51. The zip lock mechanism 51 includes a plastic slider 54 and two seams 52. The slider 54 operatively engages the plastic seams 52 between a top stopper 56 and a bottom stopper 58. The seams 54 interlock in a closed position upon engagement of the slider 54 in a first position. The seams 52 interlock in an open position upon engagement of the slider 54 in a second position.

The wearer 500 uses the re-sealable vertical aperture 50 to access his penis to urinate outside the diaper 10 as desired, making the diaper 10 useful for incontinent individuals who are sometimes able to urinate consciously and in the normal fashion, but remain desirous of the protection the diaper 10 affords in case urine is accidentally or unconsciously discharged into the diaper 10. The diaper 10 is issued in varying sizes making the diaper appropriate for use by males of different ages. The vertical aperture 50 of the diaper 10 is useful for potty training young males as well as for treating incontinence in older individuals. Thus has been outlined the more important features of the present device.

What is claimed is:

1. A male disposable incontinence diaper comprising:
   a front portion;
   a rear portion;
   a groin portion disposed between the front portion and the rear portion;
   wherein the front portion, the rear portion, and the groin portion are formed of a liquid-impervious material;
   an exterior surface;
   an interior surface opposite the exterior surface;
   a front edge;
   a rear edge opposite the front edge;
   a pair of front attachment bodies disposed on the front edge, each front attachment body disposed proximal to a corner of the front edge;
   a pair of rear attachment bodies disposed on the front edge, each rear attachment body disposed proximal to a corner of the rear edge, wherein the rear attachment bodies selectively releasably engage the front attachment bodies;
   wherein the front edge and the rear edge are configured to continuously wrap around a hip of a male human wearer upon the engagement of the front attachment bodies and the rear attachment bodies;
   an absorbent pad continuously disposed only within the front portion and the groin portion of the interior surface along a central vertical axis of the interior surface;
   a first side edge and a second side edge opposite the first side edge continuously disposed between the front portion and rear portion of the diaper;
   a corner disposed between each of the first side edge and the second side edge and each of the front edge and the rear edge;
      an amount of elastic continuously disposed within each of the first side edge and the second side edge;
   wherein the first side edge and the second side edges are configured to encircle and snuggly conform to an upper end of a wearer's legs upon the engagement of the first attachment bodies to the second attachment bodies;
   a re-sealable vertical aperture disposed along a central vertical axis of the pad proximal to the pad anterior end, the aperture comprises:
      a plastic slider that operatively engages two intermarrying plastic seams, the slider closing and sealing the seams when moved to a first position, and alternately opening and unsealing the seams when moved to a second position.

2. The male disposable incontinence diaper of claim 1 wherein the front attachment bodies are situated on the exterior surface of the diaper and the rear attachment bodies are situated on the interior surface of the diaper, the front attachment bodies fastening to the rear attachment bodies when overlapped thereon.

3. The male disposable incontinence diaper of claim 1 wherein the front attachment bodies are situated on the exterior surface of the diaper and the rear attachment bodies are situated on the interior surface of the diaper, the rear attachment bodies fastening to the front attachment bodies when overlapped thereon.

4. The male disposable incontinence diaper of claim 1 wherein the plastic slider seals the vertical aperture with the slider in an uppermost position.

5. The male disposable incontinence diaper of claim 1 wherein the plastic slider unseals the vertical aperture with the slider in a lowermost position.

6. The male disposable incontinence diaper of claim 4 wherein the plastic slider terminates in an uppermost position at a top stop device at the top of the seams.

7. The male disposable incontinence diaper of claim 5 wherein the plastic slider terminates at a bottom stop device at the bottom of the seams.

* * * * *